(12) United States Patent
Martinez Romero et al.

(10) Patent No.: US 9,486,841 B2
(45) Date of Patent: Nov. 8, 2016

(54) AUTONOMOUS MOBILE FOAM-PRODUCING UNIT FOR CLEANING

(71) Applicant: Quimica Rosmar, S.A. de C.V., Mexico City (MX)

(72) Inventors: Rodrigo Martinez Romero, Mexico City (MX); Humberto Martinez Romero, Mexico City (MX)

(73) Assignee: Quimica Rosmar, S.A. de C.V., Mexico City (MX)

( * ) Notice: Subject to any disclaimer, the term of this patent is extended or adjusted under 35 U.S.C. 154(b) by 91 days.

(21) Appl. No.: 14/424,190

(22) PCT Filed: Aug. 30, 2013

(86) PCT No.: PCT/MX2013/000104
§ 371 (c)(1),
(2) Date: Feb. 26, 2015

(87) PCT Pub. No.: WO2014/035229
PCT Pub. Date: Mar. 6, 2014

(65) Prior Publication Data
US 2015/0321228 A1    Nov. 12, 2015

(30) Foreign Application Priority Data
Aug. 31, 2012  (MX) .................. MX/u/2012/000387

(51) Int. Cl.
| | | |
|---|---|---|
| *B01F 3/04* | (2006.01) | |
| *B08B 3/00* | (2006.01) | |
| *B01F 15/02* | (2006.01) | |
| *B01F 13/00* | (2006.01) | |
| *B05B 7/24* | (2006.01) | |
| *A61L 2/235* | (2006.01) | |
| *A62C 27/00* | (2006.01) | |

(52) U.S. Cl.
CPC ............... *B08B 3/003* (2013.01); *A61L 2/235* (2013.01); *B01F 3/04446* (2013.01); *B01F 13/004* (2013.01); *B01F 15/0243* (2013.01); *B05B 7/2489* (2013.01); *A62C 27/00* (2013.01); *B01F 2215/004* (2013.01)

(58) Field of Classification Search
CPC .... B01F 3/04; B01F 3/04446; B05B 7/2489; A61C 27/00
USPC .................... 261/30, 72.1, 76, 78.2, DIG. 26
See application file for complete search history.

(56) References Cited

U.S. PATENT DOCUMENTS

| | | | |
|---|---|---|---|
| 5,582,776 A | * | 12/1996 | Crawley ................. A62C 5/02 169/15 |
| 6,279,589 B1 | | 8/2001 | Goodley |
| 7,959,091 B2 | | 6/2011 | Slone et al. |
| 2002/0127158 A1 | | 9/2002 | Holsclaw et al. |
| 2009/0194178 A1 | | 8/2009 | Slone et al. |

* cited by examiner

*Primary Examiner* — Robert A Hopkins
(74) *Attorney, Agent, or Firm* — The Webb Law Firm

(57) ABSTRACT

The present invention relates to an autonomous mobile foam-producing unit for cleaning, specifically said unit allows the cleaning and sanitization of agricultural and livestock areas. The invention also enables to generate a large quantity of foam quickly and ejected with high pressure, preventing in turn a water hammer or Zhukowski pulse. The present invention is also autonomous, including power systems based on gasoline or diesel engines with the ability to be adapted to batteries and solar cells.

5 Claims, 3 Drawing Sheets

AUTONOMOUS MOBILE FOAM-PRODUCING UNIT FOR CLEANING

CROSS-REFERENCE TO RELATED APPLICATIONS

This application is the United States national phase of International Application No. PCT/MX2013/000104 filed Aug. 30, 2013, and claims priority to Mexican Patent Application No. MX/u/2012/000387 filed Aug. 31, 2012, the disclosures of which are hereby incorporated in their entirety by reference.

FIELD OF THE INVENTION

The present invention pertains to the field of cleaning systems. Specifically, the present invention refers to an autonomous mobile foam producing unit for cleaning and sanitizing work areas.

BACKGROUND OF THE INVENTION

For cleaning in different situations it has been found and documented that having a foam-producing apparatus facilitates the cleaning process making it better and more effective. One of the fields where is necessary to have high cleanliness standards to ensure bio-security is agriculture and livestock, where has been little innovation in this matter in the past few years.

Bio-security assurance and decrease of mortality and morbidity in agricultural production is not limited to the proper use of vaccines and drugs, or to the right selection of efficient practices and processes in terms of operation of the farm for guarantee the same. The first step to achieve the health quality assurance is to incorporate to the operational practices the concept that the cleaning and sanitizing process must provide a clean work environment, an equipment in optimal sanitary conditions, all with the aim of preventing pollution and controlling diseases, microbiologically monitored.

U.S. Pat. No. 7,959,091 discloses a mobile cleaning unit that produces foam, such unit is useful for cleaning and sanitizing work areas. However, this document does not show a high foam generation capacity, as to date equipment to generate foam of prior art do it poorly derived from the complexity existing in technology for making a rich and dry mixture and displacing it for dosing at high speed. This is also derived from the fact that this unit is designed for controlled operations within an industrial plant with controlled services (electricity, water and space) and small dimensions.

One of the problems arising in agribusiness and which has not been solved through previous art resides in that in the places where the farms are located, electric service, water in the required location and air are very scarce or absent, so that portable power plants or special arrangements to reduce energy from primary lines from 440 V to the appropriate voltage are needed, and also the equipments require a controlled voltage and electricity quality, since their electric/electronic mechanisms are at risk of damage. Also they usually need water tankers to provide the amount of water needed, which can be at least 20 $cm^3$ per house, consuming a huge amount of liquid and using this tanker to carry water from a well to the farm house, covering a distance up to 5 km. And regarding to the air, this is a service not frequently used in agriculture, thus for solving this they require a compressor and the complexity of the power supply is the same.

On the other hand, for generating a quality foam is necessary to have a high pressure of air and/or water; however, such high pressure sources often cause safety problems.

Previous art has disclosed the very low capacity of foam generation, which derives from the complexity existing in technology for making a rich and dry mixture of foam and its displacement to dose at high speed. This leads to in agriculture, derived from large areas, cleaning times are become very lengthy and unproductive, since a limited time is available in cycles for the cleaning process, which would make the technology of little use.

A bad mixture of a liquid phase and a gas phase lead to when wanting to transport such mixture the speed of liquid phase and gas phase are different, which imply the well known "water hammer" that causes that due to the speed acquired by gas, equipment can be damaged or tubing can be broken.

SUMMARY OF THE INVENTION

Therefore, an object of the present invention is to provide an autonomous mobile-foam producing unit for cleaning, which allows to foam a large amount of liquid, at least 40 L/min, which in turn generates between 4 and 6 times this volume in foam, depending on how rich and dry it is needed, dosing between 150 L/min and 300 L/min of dry foam.

As well, a further object of the present invention is to provide an autonomous mobile foam-producing unit in terms of energy, water and air, so that the optimal energy and air balance is achieved to operate the various pumping equipment and foam generation, causing that in a space that has the size of a 2.5-m trailer the necessary resources can be available. Power systems are based on gasoline or diesel engines, with the ability to be adapted to batteries and solar cells.

Another object of the present invention is to provide an autonomous mobile foam-producing unit for cleaning that performs cleaning in agribusiness at a pace of 750 $m^2$ per hour, which would make that a 1500 $m^2$-standard facility be cleaned in two hours, thus allowing to cover a greater number of $m^2$ per day or reduce the number of operational staff.

A further object of the invention is to provide an autonomous mobile foam producing unit for cleaning that allows to improve the quality of the same, wherein the microbiological results allow us to check the reduction in aerobic mesophyllic and fecal coliform counts (as indicator microorganisms) with the sole use of this equipment in the cleaning process, and as a consequence it allows improving the level and life quality of animals, reducing vaccine use and animal mortality.

BRIEF DESCRIPTION OF FIGURES OF THE INVENTION

FIG. 1 relates to a foaming box picture, in which a foaming box (1), an air dosing hose (2), a foam outlet hose (3) and an inlet hose (4) is observed.

FIG. 2 relates to a foaming box picture (1), open.

FIG. 3 refers to an image of the foaming box (1), open, wherein the connection of the inlet hose (4), the air dosing hose (2), the air regulator (5) is observed, foaming chamber with fluidized bed (6) and the foam outlet hose (3).

DETAILED DESCRIPTION OF THE INVENTION

The present invention relates to an autonomous mobile foam-producing unit for cleaning in agribusiness or livestock industry.

The autonomous mobile foam producing unit for cleaning according to the present invention comprises:
  a) a trailer;
  b) a compressor with a gasoline tank;
  c) a tank container with capacity of at least 2500 L, which has a dosing orifice at its top;
  d) a centrifugal pump; and
  e) a foaming box (1) having an air dosing hose (2) connected, which in turn is connected to the compressor, a foam outlet hose (3), an inlet hose (4) connected from the tank to said foaming box, passing through the centrifugal pump; said foaming case has an air regulator (5) inside, and a foaming case with fluidized bed (6).

The dosage of detergent solution is made by the hole in the top of the tank container, the solution is directed to the centrifugal pump, then through the inlet hose (4) is directed towards the foaming box (1) specifically to the foaming chamber with fluidized bed (6), wherein the solution is mixed to produce foam.

The cleaning unit of the present invention avoids a bad mixture of the liquid phase and the solid phase, which translates in avoiding a water hammer or Zhukowski pulse despite the high velocity acquired by the gas. Thus, the present invention has achieved to overcome the foaming capacity of foaming a high amount of liquid at least of 40 L/min, which generates between 4- and 6-fold this volume in foam, depending on how rich and dry the foam is needed, dosing between 150 L/min and 300 L/min of dry foam.

To achieve this technical complexity, the unit according to the present invention success in bringing under control the following factors:
  The inlet pressure and speed of the air.
  The inlet pressure and flow of the liquid.
  The appropriate concentration of the detergent for unifying both phases.
  The capacity of the foaming chamber (6) to generate enough turbulent flow necessary to carry out, in a space of not more than 60 cm, the mixture of phases without a loss greater of 60% in pressure, since the pressure at the discharge head is at least 10 m 1 kg/cm$^2$), taking into account that both are inlet flows and they are Newtonian, and when the mixture is performed, the foam has a non-Newtonian behavior. Also the flow has a Reynolds' number Re≥2300, derived from the equation:

$$Re=\rho v_s D/\mu.$$

Flow supply is parallel or crossover, as in counter-current it causes a much greater loss or can enter to the liquid line and cause damages to the equipment or the system.
  Control of air pressures during the supply to prevent that the pressure of any of the fluids obstructs the flow of the other and hinder the proper mixture.
  Transportation of foam along pipeline or flexible hoses up to 100 m long and diameters of ½ inch to 1 inch for direct application to the surfaces of the area to be cleaned.

Figure 1:
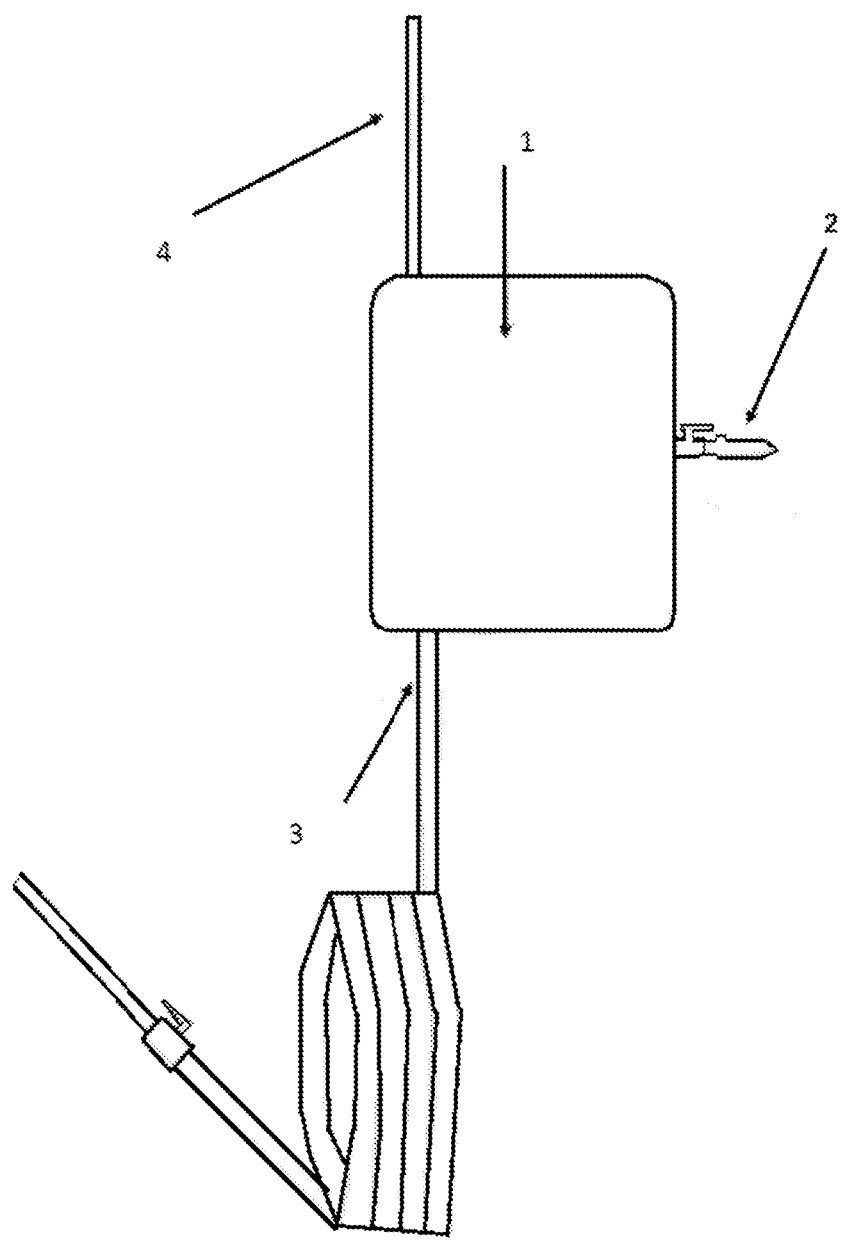
FIG. 1 depicts the foaming box (1) having connected a foam outlet hose (3), wherein said hoses can measure up to 100 meter, and an inlet hose (4), which carries the detergent solution from the tank container to the foaming chamber with fluidized bed.
Figure 2:
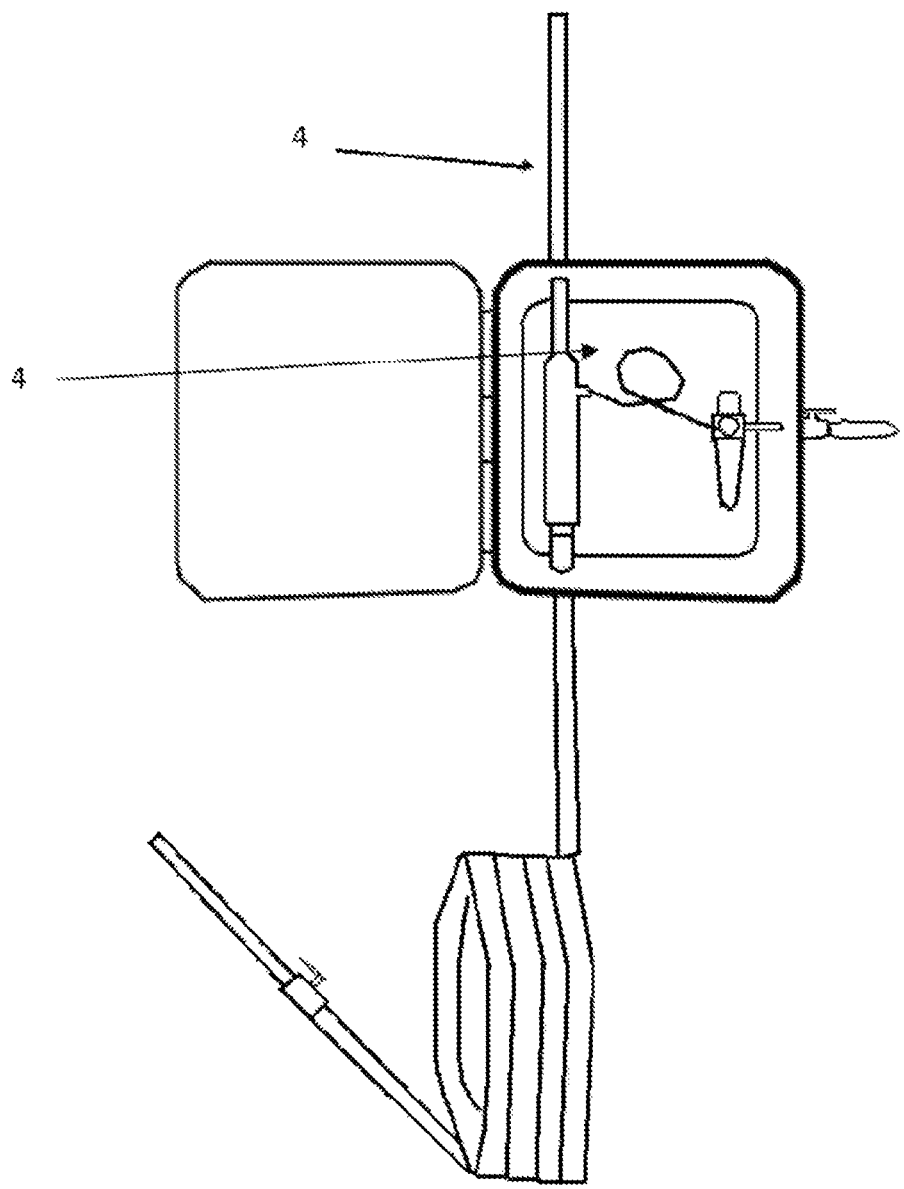
FIG. 2 depicts the interior of the foaming box (1) where the connection of the inlet hose (4) with the foaming chamber with fluidized bed (6) is observed.
Figure 3:
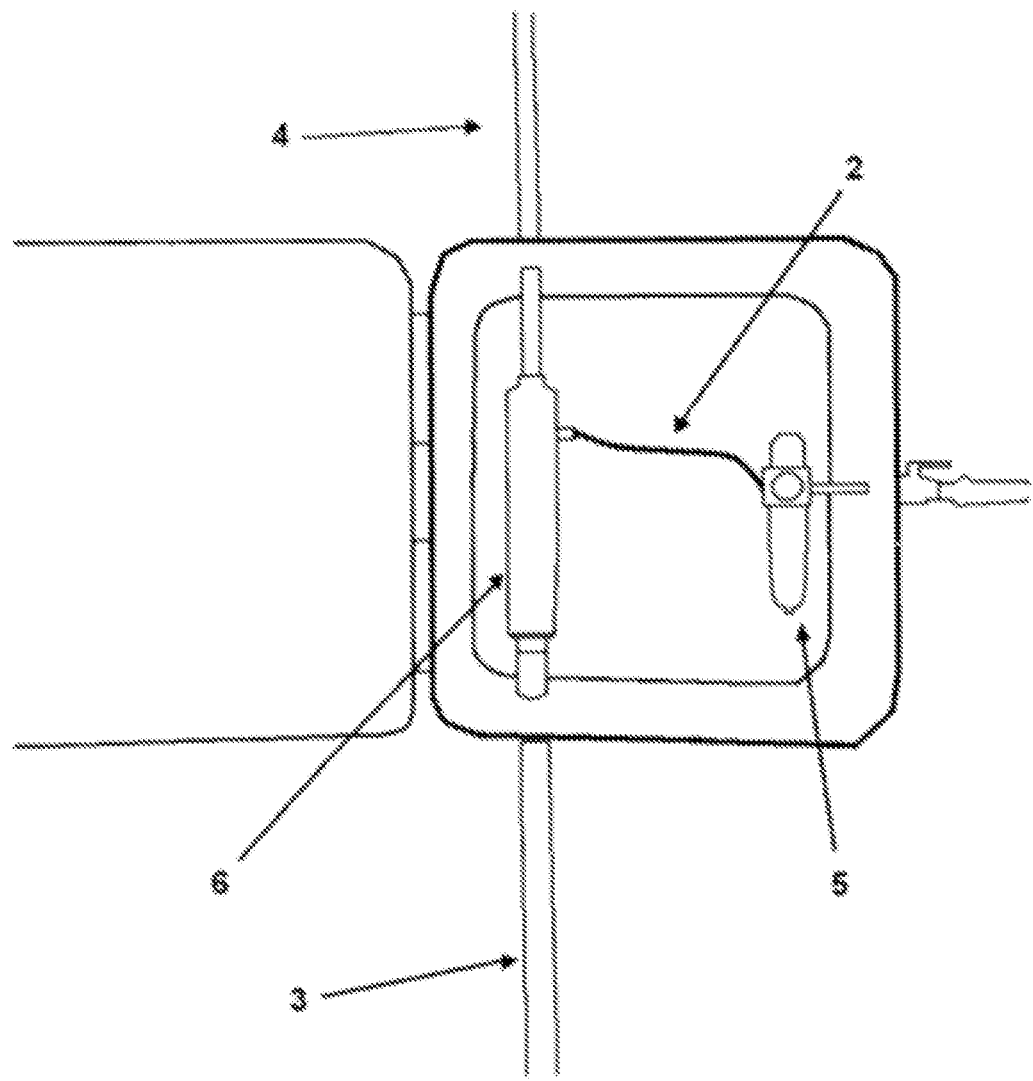

In FIG. 3 the inlet hose (4) through which the detergent solution passes to then continue to the foaming chamber with fluidized bed (6) wherein said chamber (6) allows to generate the necessary turbulence along with the air supplied through the air dosing hose (2) to obtain a suitable mixture of air and water, thus preventing that the water pressure blocks the air pressure or vice versa and avoiding a reflux, but allowing the outlet hose (3) to generate enough foam also with sufficient pressure. As well, the foaming chamber with fluidized bed (6) is able to equalize the speed at which the mixing takes place.

This innovation provides autonomy in energy, water and air, so that the right balance of energy and air to operate the various pumping equipment and foam generation is achieved, making available the necessary resources in a space with the size of a 2.5-m trailer. Power systems are based on gasoline or diesel engines with the ability to be adapted to batteries and solar cells.

The use of the cleaning unit according to the present invention has been shown to significantly decrease mortality of farm animals and thus the costs of vaccines and drugs, helping to improve overall production costs in an industry with very reduced margins, succeeding in moving from extreme cases with 17% mortality to <5%. Microbiological results in usual cleaning processes with any of the current equipment or techniques are: Floors 2,200 CFU/cm$^2$ of aerobic mesophyllic and <10 CFU/cm$^2$ of fecal coliform; In feeder 1800 CFU/cm$^2$ of aerobic mesophyllic and 50 CFU/cm$^2$ of fecal coliform. Using the cleaning unit the results in the same sampling points were: Floors 23,000 CFU/cm$^2$ of aerobic mesophyllic and 180 CFU/cm$^2$ of fecal coliform; in feeder 720 CFU/cm$^2$ of aerobic mesophyllic and <10 CFU/cm$^2$ of fecal coliform. Thus, for aerobic mesophyllic bacteria a 1-log decrease is observed with the use of the cleaning unit according to the present invention and up to 2-log decrease of fecal coliform, so that it is shown how cleansing achieved with the foam is extremely effective to allow the detergent having more time to act on surfaces and more effectively remove dirt.

Having disclosed the invention, what is contained in the following claims is claimed as property:

1. An autonomous mobile dry foam-producing unit for cleaning, wherein it allows to foaming a large amount of liquid such that achieves an optimal balance of energies and air in the generation of dry foam, thus improving the quality of the dry foam; said unit comprises:
  a) a trailer;
  b) a compressor with a gasoline tank;
  c) a tank container having a capacity of at least 2500 L of detergent solution;
  d) a centrifugal pump;
  e) a foaming box (1) having inside an air regulator (5) and a foaming chamber with fluidized bed (6) connected to each other; said foaming chamber (6) allows to equalize the speeds at which a mixture of detergent solution and air is carried out, wherein said foaming chamber (6) also prevents a water hammer or Zhukowski pulse during the production of the dry foam;

f) an inlet hose for detergent solution (4), which starts from the tank container, goes to the centrifugal pump and connects at the top side of the foaming chamber (6);

g) an air dosing hose (2), connected to the compressor at one end and at the other end to the air regulator (5) located inside the foaming box; and h) an outlet hose having a length of 100 m and a diameter of 0.5 inches to 1 inch, which is connected at the bottom of the foaming chamber (6).

2. An autonomous mobile dry foam-producing unit for cleaning according to claim 1, wherein the foaming chamber (6) allows to generate the necessary turbulence along with the air supplied through the air dosing hose (2) to obtain a proper air-water mixture, thus avoiding that the water pressure blocks the air pressure or vice versa, avoiding a reflux, but allowing the foam outlet hose (3) to generate sufficient foam also with a sufficient pressure.

3. An autonomous mobile dry foam-producing unit for cleaning according to claim 2, wherein the foaming chamber (6) also allows the phase mixture without a loss of pressure greater than 60%.

4. An autonomous mobile dry foam-producing unit for cleaning according to claim 3, wherein the foaming chamber (6), the air flow supply and the flow of detergent solution is performed in parallel or crossover.

5. An autonomous mobile dry foam-producing unit for cleaning according to claim 1, wherein said unit allows foam production in the order of 150 L/min to 300 L/min.

\* \* \* \* \*

UNITED STATES PATENT AND TRADEMARK OFFICE
CERTIFICATE OF CORRECTION

PATENT NO. : 9,486,841 B2  
APPLICATION NO. : 14/424190  
DATED : November 8, 2016  
INVENTOR(S) : Rodrigo Martínez Romero et al.

Page 1 of 1

It is certified that error appears in the above-identified patent and that said Letters Patent is hereby corrected as shown below:

On the Title Page

Column 2, Item (57) ABSTRACT, Line 6, delete "Zhukowski" and insert -- Zhukovsky --

In the Claims

Column 4, Line 66, Claim 1, delete "Zhukowski" and insert -- Zhukovsky --

Signed and Sealed this
Fourteenth Day of February, 2017

Michelle K. Lee
*Director of the United States Patent and Trademark Office*